(12) United States Patent
Rajewski et al.

(10) Patent No.: US 7,744,923 B2
(45) Date of Patent: Jun. 29, 2010

(54) METHOD FOR PRECIPITATION OF SMALL MEDICAMENT PARTICLES INTO USE CONTAINERS

(75) Inventors: Roger A. Rajewski, Lawrence, KS (US); Bala Subramaniam, Lawrence, KS (US); Fenghui Niu, Lawrence, KS (US)

(73) Assignee: Crititech, Inc., Lawrence, KS (US)

( * ) Notice: Subject to any disclaimer, the term of this patent is extended or adjusted under 35 U.S.C. 154(b) by 0 days.

(21) Appl. No.: 11/870,554

(22) Filed: Oct. 11, 2007

(65) Prior Publication Data

US 2008/0089944 A1 Apr. 17, 2008

Related U.S. Application Data

(60) Provisional application No. 60/829,082, filed on Oct. 11, 2006.

(51) Int. Cl.
*A61K 9/14* (2006.01)

(52) U.S. Cl. .................................................... 424/489
(58) Field of Classification Search ................... None
See application file for complete search history.

(56) References Cited

U.S. PATENT DOCUMENTS

| | | | |
|---|---|---|---|
| 5,043,280 | A | 8/1991 | Fischer et al. |
| 5,424,076 | A | 6/1995 | Gorissen et al. |
| 5,801,106 | A * | 9/1998 | Jameson ..................... 442/334 |
| 5,833,891 | A | 11/1998 | Subramaniam et al. |
| 5,851,453 | A | 12/1998 | Hanna et al. |
| 5,981,474 | A | 11/1999 | Manning et al. |
| 6,063,138 | A * | 5/2000 | Hanna et al. ............... 23/295 R |
| 6,113,795 | A | 9/2000 | Subramaniam et al. |
| 6,299,906 | B1 | 10/2001 | Bausch et al. |
| 6,440,337 | B1 | 8/2002 | Hanna et al. |
| 6,576,262 | B1 | 6/2003 | Hanna et al. |
| 6,620,351 | B2 | 9/2003 | Gupta et al. |
| 6,860,907 | B1 | 3/2005 | Hanna et al. |
| 7,087,197 | B2 | 8/2006 | Palakodaty et al. |
| 7,115,280 | B2 | 10/2006 | Hanna et al. |
| 7,404,943 | B2 * | 7/2008 | Eckert et al. ................. 423/489 |

FOREIGN PATENT DOCUMENTS

| | | |
|---|---|---|
| EP | 0 949 203 A1 | 10/1999 |
| WO | WO 99/44733 | 9/1999 |
| WO | WO 01/15664 A2 | 3/2001 |
| WO | WO 2004/062785 A1 | 7/2004 |
| WO | WO 2004/098561 A2 | 11/2004 |

* cited by examiner

*Primary Examiner*—Humera N Sheikh
(74) *Attorney, Agent, or Firm*—Rick Matus; Innovar, L.L.C.

(57) ABSTRACT

Commercially feasible methods for lyophobic precipitation of liquid-dispersed or dissolved material (e.g., medicaments) are provided wherein a plurality of individual, open containers (22) each containing a quantity (84) of a solution or dispersion are treated within a common pressurizable chamber (12). In this process, desired near-supercritical or supercritical temperature and pressure conditions are established for a selected antisolvent gas such as carbon dioxide, and an ultrasonic device (14) is actuated to generate high energy ultrasonic waves in the chamber (12). This leads to intense mixing of the antisolvent with the liquid solution or dispersion within the containers (22), with consequent solvent removal and material precipitation.

34 Claims, 1 Drawing Sheet

METHOD FOR PRECIPITATION OF SMALL MEDICAMENT PARTICLES INTO USE CONTAINERS

BACKGROUND OF THE INVENTION

1. Field of the Invention

The present invention is broadly concerned with improved, commercially feasible methods for the simultaneous precipitation of material (particularly medicaments) within a plurality of containers using near-supercritical or supercritical antisolvent gas such as carbon dioxide.

2. Description of the Prior Art

U.S. Pat. No. 5,833,891 describes greatly improved methods for the precipitation of particles such as medicaments using near-supercritical or supercritical antisolvents. These methods generally involve spray techniques wherein the interphase mass transfer rate is maximized between small droplets of the dispersion and antisolvent gas so as to generate very small precipitated particles. This patent also teaches that medicaments can be prepared and administered to a patient without the necessity of transferring the medicament between containers. That is, a dispersion/antisolvent precipitation is carried out in a final use container which is consequently sealed to permit later withdraw of medicament doses from the use container. This technique generally involves lyophobic precipitation of medicaments on a batch or semi-batch basis. However, the methods taught for this process involve use of long glass tubes sealed at one end with glass frits. Such fritted tubes are not at all suitable for commercial production of medicaments, and thus the specific single vial techniques described in the '891 patent are of limited commercial potential.

U.S. Pat. No. 6,620,351 is also concerned with formation of nanoparticles using supercritical fluid antisolvents. In this case, a dispersion containing a desired material to be precipitated is applied on or very close to an ultrasonic vibrating surface to generate small droplets. An antisolvent at near-supercritical or supercritical conditions is also applied adjacent the vibrating surface in order to precipitate the desired particles. Here again, the requirement for direct or near contact between the ultrasonic vibrating surface and the material-containing dispersion means that the process cannot be effectively used on a commercial scale. This is because containers would need to be individually treated, or an individual vibratory surface would need to be provided for each container. In either case, the cost and complexity of such a system would materially detract from the usefulness of the process.

SUMMARY OF THE INVENTION

The present invention overcomes the problems outlined above and provides greatly improved and commercially feasible methods allowing the simultaneous precipitation of liquid-dispersed or dissolved material within a plurality of individual containers or vials using antisolvent gas at near-supercritical or supercritical conditions. The methods are similar to those disclosed in U.S. Pat. No. 5,833,891, incorporated by reference herein. The present method broadly involves locating a plurality of containers within a common pressurizable chamber, each container being at least partially open to the atmosphere within the chamber and having a quantity of a liquid solution or dispersion therein containing material to be precipitated. The chamber is then heated and pressurized with the containers therein, including the step of introducing the antisolvent gas into the chamber. When appropriate temperature and pressure conditions exist within the chamber (generally near-supercritical or supercritical conditions for the selected antisolvent), ultrasonic energy waves are generated within the antisolvent in order to cause the antisolvent to rapidly mix with and dissolve the liquid therein and precipitate the material as the small particles.

In one embodiment, each of the containers has a stopper loosely fitted within a mouth thereof during the solvent removal/precipitation step. Thereafter, each of the valves is sealed by fully installing each of the stoppers into the container mouths. This is preferably accomplished by a stoppering apparatus situated within the chamber.

As noted, it is preferred that the temperature and pressure conditions within the chamber be at or near-supercritical or supercritical conditions for the antisolvent, and generally from about $0.7$-$1.4\,T_c$ and from about $0.2$-$7\,P_c$ for the antisolvent. More normally, the pressure will be less than $2\,P_c$ for a given chamber temperature. Preferably, once the composition of the solution or dispersion is known, simple experiments can be undertaken to ascertain optimum temperature and pressure conditions that achieve maximum mixing between antisolvent and solution or dispersion while preventing overflow of liquid from the individual containers.

The preferred antisolvents are selected from the group consisting of carbon dioxide, propane, butane, ethane, isobutane, nitrous oxide, sulfur hexafluoride, trifluoromethane, xenon, and mixtures thereof. Generally, carbon dioxide is the single most preferred antisolvent. The compositions treated in the invention are preferably true solutions made up of a solvent and a solute comprising a material to be precipitated. Alternatively, the composition maybe a dispersion with the dispersant comprising the material to be precipitated. Normally, the solution or dispersion should contain at least 5% by weight solute or dispersant, more preferably at least about 50% by weight solute or dispersant, and most preferably at least about 90% by solute or dispersant. The solution or dispersion may also contain other auxiliary ingredients such as adjuvants (in the case of medicaments), excipients, surface active agents, extenders, binders, and the like.

The ultrasonic energy waves are preferably generated by the use of an ultrasonic probe located within the chamber at a position relatively remote from the individual containers. It has been found that even when the containers are partially stoppered, the ultrasonic waves can nonetheless enter the containers to mix with the liquid therein and effect particle precipitation. The precipitated materials can be in a variety of forms, e.g., pure crystalline or non-crystalline particles of the material or a cake containing the material along with one or more of auxiliary ingredients.

In one embodiment, the resultant material is in the form of particles having an average diameter of from about $0.1$-$10\,\mu m$ and more preferably up to about $0.6\,\mu m$.

DETAILED DESCRIPTION OF THE PREFERRED EMBODIMENT

Figure 1:
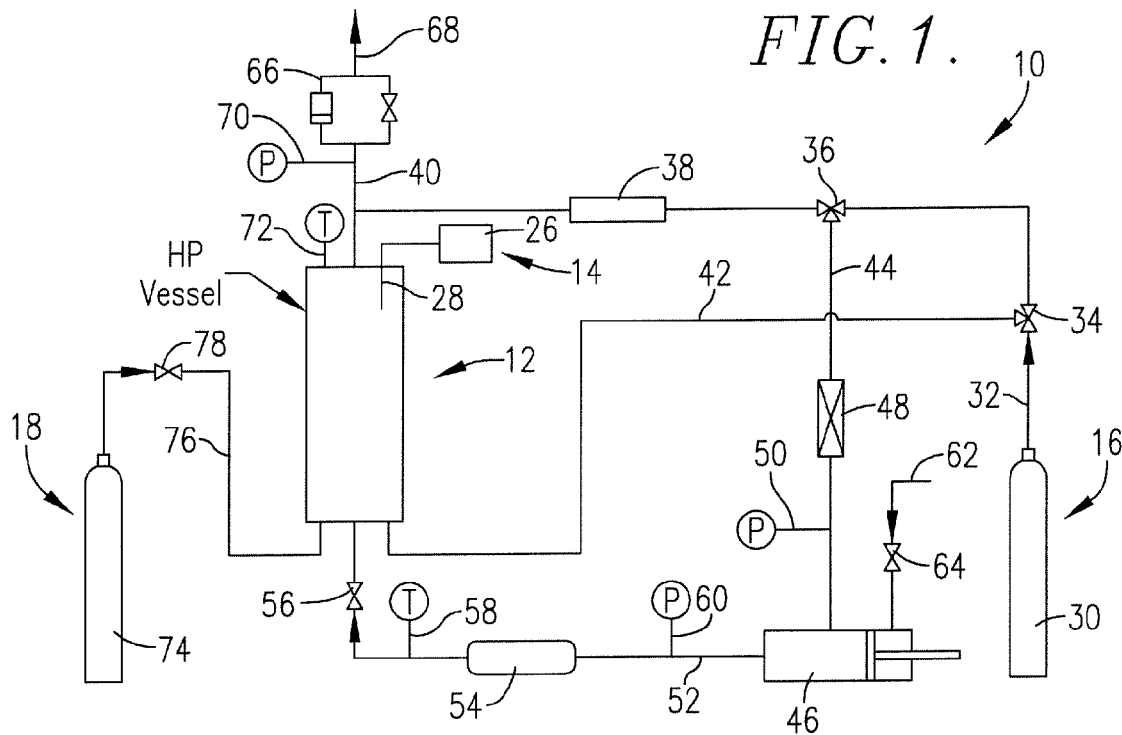
FIG. 1 is a schematic representation of a precipitation apparatus useful in the present invention.

Turning to the drawings, in greater detail, and initially to FIG. 1, an exemplary precipitation apparatus useful in the context of the invention is represented generally by the numeral 10. Broadly speaking, the apparatus 10 includes a high pressure chamber 12 equipped with an ultrasonic transducer device 14, a system 16 for the introduction of antisolvent into chamber 12, and a test system 18.

In one embodiment, the chamber 12 is an upright metallic vessel of appropriate volume (e.g., 6 L) having two viewing windows (not shown). The chamber also includes an internal shelf 20 adapted to hold a plurality of containers or vials 22. Additionally, a stoppering mechanism 24 is situated above shelf 20 for purposes to be described. The device 14 includes an external ultrasonic transducer 26 operably coupled with a probe 28 within chamber 12.

The antisolvent system 16 includes a gas cylinder 30 designed to hold a supply of antisolvent gas, with a line 32 having valves 34 and 36 and moisture trap 38 interposed therein. As shown, the line 32 intersects an outlet conduit 40 leading from chamber 12. A bypass line 42 extends from valve 34 to the bottom of chamber 12, and a delivery line 44 extends from valve 36 to booster pump 46; the line 44 is also equipped with a filter 48 and a pressure indicator 50. The output from pump 46 is delivered via line 52 having a 4.5 L surge tank 54, valve 56, and temperature and pressure indicators 58 and 60 therein. As shown, the line 52 is coupled with the base of chamber 12 for delivery of antisolvent gas into the chamber. An air line 62 having valve 64 therein is also coupled with pump 46.

A safety valve 66 is operably coupled with conduit 40 and has a vent 68. Pressure and temperature indicators 70 and 72 are respectively coupled with conduit 40 and chamber 12.

The system 18 is optional and comprises a gas cylinder 74 coupled with a line 76 having a valve 78 therein. The cylinder 74 normally holds a supply of nitrogen which is used to test the leak integrity of the chamber 12 and associated components, prior to actual use thereof.

The containers 22 are entirely conventional and for purposes of illustration are shown with open mouths 80, and stoppers 82 loosely fitted within the mouths 80 so that the interior of the containers communicate with the atmosphere within chamber 12. As shown, each valve contains a quantity 84 of a liquid solution or dispersion having therein the material to be precipitated. After precipitation (FIG. 3), a quantity 86 of precipitated material is present in each of the containers 22.

Figure 3:
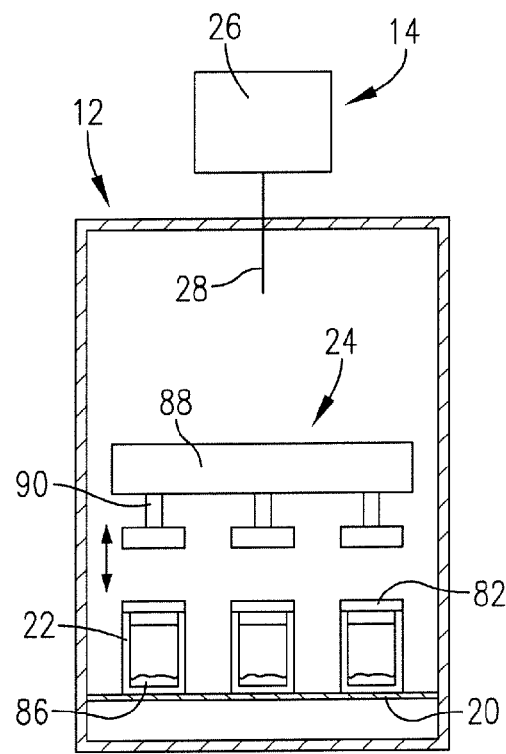

The stoppering device 24 is schematically illustrated and contains a common header 88 with a series of depending, reciprocal plungers 90 respectively situated above each stopper 82. The plungers 90 are operable to engage the respective stoppers 82 to fully seat the latter within the container mouths 80 as illustrated in FIG. 3.

Figure 2:
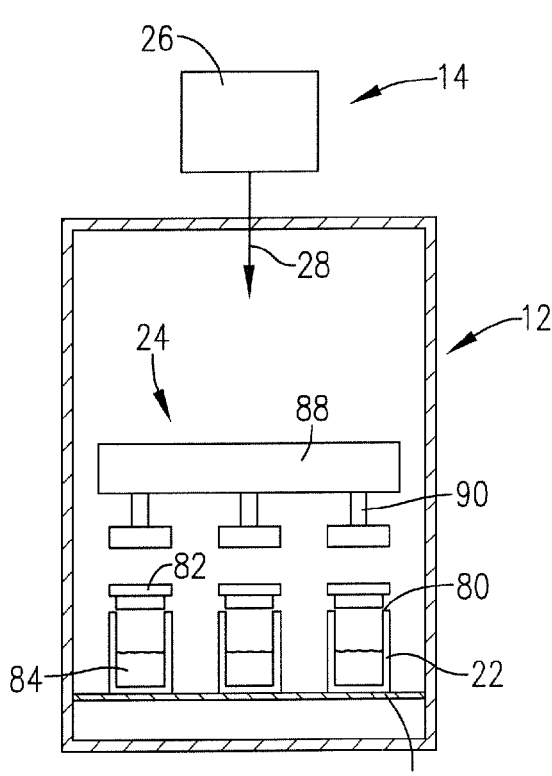
FIG. 2 is a schematic view of the pressure vessel forming a part of the FIG. 1 apparatus, illustrating a plurality of open containers therein each containing a quantity of a liquid dispersion including material to be precipitated.

During use of apparatus 10, the latter is first heated to a specified temperature using a conventional heating tap coupled with a controller (not shown). The entire system is then tested for leakage using nitrogen system 18. Following testing, a plurality of containers 22 each having a quantity 84 of the liquid solution or dispersion are placed on shelf 20 below the individual plungers 90. The containers 22 are partially stoppered as shown in FIG. 2, such that the interior of the containers communicate with the chamber atmosphere. At this point, the chamber 12 is pressurized by introduction of antisolvent gas from cylinder 30 into vessel 16. This involves opening of valves 34, 36 and 56 to permit antisolvent to flow through filter 48, booster pump 46 and surge tank 54 into the interior of the vessel. The antisolvent gas is recycled through conduit 40 and lines 32, 44 and 52, and moisture is removed by trap 38.

Once the vessel 12 is fully pressurized and the temperature and pressure conditions therein have reached desired stabilized levels for the antisolvent employed, the device 14 is actuated in order to generate ultrasonic energy waves within the antisolvent in chamber 12. These waves propagate throughout the interior of the chamber and pass into the individual containers 22 past the loosely-fitted stoppers 82. This effects intense mixing of the antisolvent and the solution or dispersion within each of the containers 20 so that the solutions or dispersions become supersaturated and the solute or dispersant is selectively extracted into the antisolvent. This effects precipitation of the material within the containers. The precipitated material may be in various forms, including small particles in crystalline form or non-crystalline form, and an amorphous mass. If auxiliary ingredients are used, these generally precipitate along with the active ingredient. During this step, temperature and pressure conditions are carefully maintained so as to eliminate the possibility of overflow of the liquid from the containers 22 with consequent loss of material.

After the material has fully precipitated, the device 14 is left running for a period of 60-90 minutes with flowing antisolvent through chamber 12 and venting via vent 68. This assures that all residual liquid solvent or dispersion medium is removed from the containers. Thereafter, the high-pressure antisolvent is drained from the chamber 12 through vent 68 and the vessel is cooled to ambient. At this point, the stoppering apparatus 24 is employed to fully stopper each of the valves 82 (FIG. 3) to complete the process. If desired, the system can then be flushed by switching valve 34 to the line 42 and directing a fresh fluid such as $CO_2$, or another inert gas, into chamber 12. Preferably, the fluid is sterile.

The following examples set forth preferred techniques for the precipitation of particles of material in accordance with the invention. It is to be understood, however, that these examples are provided by way of illustration and nothing therein should be taken as a limitation upon the overall scope of the invention.

In Examples 1-3 below, the lyophobic precipitation of acetaminophen, ibuprofen, hydrocortisone, phenyloin, and insulin using supercritical $CO_2$ antisolvent and ultrasonic energy was investigated using apparatus of the type illustrated in FIG. 1.

The precipitation apparatus 10 included a high-pressure 6 L chamber 12 along with an ultrasonic transducer device 14 attached to the top inside of the chamber. Two view windows were provided in the chamber walls to allow visual inspection of the process. A platform 20, sized to hold up to 10 small containers 22, was located in the bottom of the chamber at approximately the base of the viewing windows. A 4.5 L surge tank 54 was used to control the fluctuation of $CO_2$ flow from the $CO_2$ pump 46, and a moisture trap 38 with desiccant was used to keep moisture out of the system. The maximum allowable pressure for the system was about 2,000 psi at a temperature of up to about 70° C.

In a typical lyophilization experiment, a number of containers 22, each containing a drug in solution, were loaded onto the platform 20 within chamber 12. The chamber was heated to a given temperature, and the entire system was tested for leakage using nitrogen gas test system 18. LabView program software was used to monitor and record the temperatures and pressures during the lyophilization/precipitation process.

After the nitrogen leak test, the chamber 12 was pressurized to a given pressure with $CO_2$. When the specified temperature and pressure set points were attained and stabilized, the ultrasonic transducer device 14 was powered to effect intense mixing of the drug solution with $CO_2$ within the containers 22. The pressure, temperature and ultrasonic energy were monitored to avoid overflow of the expanded drug solutions from the containers. It was found that preferred pressure and temperature values could be determined based upon the particular solvent used in the system. Once the drug was observed to precipitate and the solvent was extracted into the dense $CO_2$ phase, the system parameters (ultrasonic energy, temperature, pressure, $CO_2$ flow) were maintained for an additional 60-90 minutes to remove residual solvent from the containers. Preferably, the chamber 12 was then flushed with additional $CO_2$ to remove the evaporated solvent, and to effect drying of any residual solvent from the drug. The chamber 12 was then carefully depressurized and the containers containing the precipitated drugs were retrieved and cooled to ambient temperatures. Specific experimental parameters are given below.

Example 1

First Lyophobic Precipitation Experiment Using Sonicator

Drug solutions of varying concentrations in ethanol were prepared according to the table below.

| Container | Drug | Concentration mg/mL, ethanol | Drug Amount, mg |
|---|---|---|---|
| 1 | Acetaminophen | 50 | 99 |
| 2 | Acetaminophen | 90 | 179 |
| 3 | Acetaminophen | 30 | 61 |
| 4 | Ibuprofen | 50 | 105 |

2 mL of each test solution were transferred into a container. The containers were transferred to the platform inside the chamber. The chamber was then pressurized to 1200 psi using $CO_2$, and the chamber was heated to about 62-66° C. to establish supercritical conditions. The ultrasonic transducer was then powered to about 15-70% power for about 38 minutes, during which time the drug was observed to precipitate. The power was maintained at about 50% for an additional 52 minutes to remove residual ethanol from the drug. The results are shown below.

| Container | Drug | Evaporation time, min | Weight loss, wt % |
|---|---|---|---|
| 1 | Acetaminophen | 38 | 5.1 |
| 2 | Acetaminophen | 38 | 2.2 |
| 3 | Acetaminophen | 30 | 6.6 |
| 4 | Ibuprofen | N/A | N/A |

From this experiment, it was determined that drying time of a drug solution is only slightly related to the drug concentration, if at all.

Example 2

Second Lyophobic Precipitation Experiment Using Sonicator

Drug solutions of varying concentrations in ethanol, or hexafluoro-2-proponal (HFIP), were prepared according to the table below.

| Container | Drug | Concentration mg/mL, ethanol | Amount Drug mg/mL solvent |
|---|---|---|---|
| 1 | Acetaminophen | 104 | 104/1 |
| 2 | Acetaminophen | 100 | 58/0.58 |
| 3 | Hydrocortisone | 12.5 | 25/2 |
| 4 | Acetaminophen | 68 | 17/0.25 |
| 5 | Phenytoin | 13.6 | 27/2 |
| 6 | Insulin | 29 (in HFIP) | 9/0.3 |

Varying amounts of each drug solution according to the table above were transferred to designated containers. The containers were then placed on the platform in the chamber. The chamber was pressurized to 1,200 psi using $CO_2$, and the chamber was heated to about 50° C. to establish supercritical conditions. The ultrasonic transducer was powered to about 15-40% power for about 60 minutes during which time the drug was observed to precipitate and the solvent evaporated into the $CO_2$. The power was maintained at about 40-50% for an additional 90 minutes to remove residual solvent from the drug until dry. The results are shown below.

| Container | Drug | Evaporation time, min | Weight loss, wt % |
|---|---|---|---|
| 1 | Acetaminophen | 60 | 6.1 |
| 2 | Acetaminophen | 60 | 3.4 |
| 3 | Hydrocortisone | 60 | 5.6 |
| 4 | Acetaminophen | 60 | 4.1 |
| 5 | Phenytoin | 60 | 11 |
| 6 | Insulin | 60 | 0 |

From this experiment, it was determined that insulin is easily expanded, and some precipitation was observed even before the ultrasonic transducer was turned on. The acetaminophen was observed to precipitate as crystals and the phenytoin was observed to precipitate as needle-shaped crystals.

Example 3

Third Lyophobic Experiment Using Sonicator

Drug solutions of varying concentrations in ethanol or HFIP were prepared according to the table below.

| Container | Drug | Concentration mg/mL, ethanol | Amount Drug mg/mL solvent |
|---|---|---|---|
| 1 | Acetaminophen | 100 | 27/0.27 |
| 2 | Phenytoin | 14 | 13/0.9 |
| 3 | Insulin | 34 (in HFIP) | 17/0.5 |

Varying amounts of each drug solution according to the table above were transferred to designated containers. The containers were transferred onto the platform in the chamber. The chamber was pressurized to 1,200 psi using $CO_2$, and the vessel was heated to about 50° C. to establish supercritical conditions. The ultrasonic generator was programmed to be on for 1 second, off for 2 seconds, and the power supply was incrementally increased until the drug was fully precipitated, and the solvent evaporated. The power supply was at 15% for about 10 minutes, increased to 20% for about 65 minutes, increased to 24% for about 35 minutes, increased to 28% for about 40 minutes and finally increased to 30% for about 185 minutes, for a total of 5 hours and 30 minutes to complete the process. The power was then maintained at about 40% for an additional 50 minutes to remove residual solvent from the drug until dry. The results are shown below.

| Container | Drug | Evaporation time, min | Weight loss, wt % |
|---|---|---|---|
| 1 | Acetaminophen | 110 | 3.8 |
| 2 | Phenytoin | 330 | N/A |
| 3 | Insulin | 330 | N/A |

The precipitated drug particles from this experiment were observed to be larger in size than particles produced in the previous two experiments. Insulin, in particular, was observed to be much larger as precipitated in experiment three, than in experiment two. From this it was concluded that processing time correlates with particle size. Thus, shorter processing time results in smaller drug particle size.

From the following example, the significant advantages of the present invention over conventional mechanical mixing are illustrated.

Example 4

Lyophobic Precipitation Using an Air-Actuated Mixing Platform

In this experiment, an air-actuated shaker was employed in an attempt to effect lyophobic precipitation in a supercritical $CO_2$ environment via mechanical mixing. A platform was located in the high-pressure chamber at approximately the base of the viewing windows and the containers containing the drug solution were placed on the platform. Compressed air was used to shake the platform in a horizontal plane such that the contents of the container were swirled without being spilled due to motion.

Two containers were each filled separately with 1 mL of a saturated drug solution and placed on the mixing platform in the vessel. The first container contained phenyloin in acetone and the second container contained hydrocortisone in acetone. The temperature of the vessel was varied between 36 and 63° C. and the vessel was pressurized with $CO_2$ to near/supercritical, about 910-1,220 psi. The shaking time required to precipitate the drugs was up to forty-four (44) hours.

The initial experiment showed that the level of saturated solution of drug and acetone stayed virtually the same even after mechanical shaking for about 4-5 hours. While a clear meniscus was observed between the $CO_2$ and the drug solution at higher temperatures of about 48-63° C., no clear meniscus was observed at the lower temperatures of about 36-42° C. However, even after about 42-44 h, only 1 mL of the solvent had evaporated, even at higher temperatures.

From this it was concluded that the drug solution/$CO_2$ interface could not be sufficiently disturbed by the mechanical shaking to cause intense mixing between the two phases, and that severe transport limitations exist for solvent diffusion into the $CO_2$ phase.

We claim:

1. A method of simultaneous precipitation of material within a plurality of containers using an antisolvent gas, said method comprising:
    locating a plurality of containers within a pressurizable chamber, each container being at least partially open to the atmosphere within the chamber and having a quantity of a liquid therein containing material to be precipitated;
    heating and pressurizing said chamber with said containers therein;
    introducing an antisolvent gas into the chamber and establishing temperature and pressure conditions within said chamber that are at near-supercritical or supercritical conditions for said antisolvent gas thereby forming near-supercritical or supercritical, respectively, antisolvent;
    then with an ultrasonic device remote from the liquid containing material to be precipitated, generating ultrasonic energy waves within said near-supercritical or supercritical antisolvent in said chamber and propagating said waves through said near-supercritical or supercritical antisolvent in the interior of said chamber and into said containers, in order to mix said liquid and said near-supercritical or supercritical antisolvent, supersaturate the liquid with the material to be precipitated, dissolve the liquid in the near-supercritical or supercritical antisolvent, and precipitate the material as particles in said containers; and
    removing said near-supercritical or supercritical antisolvent and liquid from said chamber and said containers, thereby leaving said particles in said containers.

2. The method of claim 1, wherein each of said containers has a stopper loosely fitted within a mouth thereof during said removing, said method further comprising sealing each of said containers by fully installing each of said stoppers into said container mouths, after said removing.

3. The method of claim 1, further comprising flowing additional near-supercritical or supercritical antisolvent through the chamber after precipitation of the material as particles in said containers.

4. The method of claim 1, wherein said near-supercritical or supercritical conditions include a temperature of about 0.7-1.4 $T_c$ and a pressure of 0.2-7 $P_c$ for said antisolvent.

5. The method of claim 4, wherein said material comprises a medicament.

6. The method of claim 1, wherein said antisolvents is selected from the group consisting of carbon dioxide, propane, butane, ethane, isobutane, nitrous oxide, sulfur hexafluoride, trifluoromethane, xenon, and mixtures thereof.

7. The method of claim 1, further comprising reducing the pressure within said chamber to approximately atmospheric after removing said liquid from said containers.

8. The method of claim 1, wherein said supercritical or near-supercriticial conditions are maintained so as to prevent any substantial overflow of material from said containers during said removing.

9. The method of claim 1, wherein said particles have an average diameter of 0.1-10 μm.

10. The method of claim 9, wherein said average diameter is up to 0.6 μm.

11. The method of claim 1, wherein said material comprises a medicament.

12. The method of claim 1, wherein said material comprises at least 5% by weight of said liquid.

13. The method of claim 1, wherein said material comprises at least 50% by weight of said liquid.

14. The method of claim 2, further comprising flushing the containers with a fluid or inert gas after said removing and before said sealing.

15. The method of claim 14, wherein the flushing is conducted for a period of 60-90 minutes.

16. The method of claim 1, wherein said material is a medicament, and said liquid comprises an auxiliary ingredient selected from the group consisting of adjuvants, excipients, extenders, surface active agents, binders and a combination thereof.

17. The method of claim 16, wherein said auxiliary ingredient precipitates in said particles with said medicament.

18. The method of claim 1, wherein said supercritical conditions include a temperature of 0.7-1.4 $T_c$ and a pressure of 0.2-7 $P_c$ for said antisolvent.

19. The method of claim 18 further comprising flowing additional near-supercritical or supercritical antisolvent through the chamber after precipitation of the material as particles in said containers.

20. The method of claim 19 further comprising flushing the chamber with a fluid or inert gas following said removing.

21. The method of claim 20 further comprising reducing the pressure within said chamber to approximately atmospheric after said removing.

22. The method of claim 18, wherein said material comprises a medicament.

23. The method of claim 22, wherein said liquid further comprises an auxiliary ingredient selected from the group consisting of adjuvant, excipient, extender, surface active agent, binder and a combination thereof.

24. The method of claim 18, wherein said antisolvent is selected from the group consisting of carbon dioxide, propane, butane, ethane, isobutane, nitrous oxide, sulfur hexafluoride, trifluoromethane, xenon, and mixtures thereof.

25. The method of claim 18, wherein said particles have an average diameter of about 0.1-10 µm.

26. The method of claim 18, wherein said material comprises at least 5% by weight of said liquid.

27. The method of claim 18, wherein each of said containers has a stopper loosely fitted within a mouth thereof during said removing, said method further comprising sealing each of said containers by installing each of said stoppers into said container mouths after said removing.

28. A method for the simultaneous formation of particles within plural containers, the method comprising:
   locating plural containers within a pressurizable chamber, each container being at least partially open to the atmosphere within the chamber and having a quantity of a liquid therein, said liquid comprising liquid carrier and material to be precipitated;
   heating and pressurizing said chamber;
   introducing an antisolvent for the material into the chamber and establishing temperature and pressure conditions within said chamber that are at near-supercritical or supercritical conditions for said antisolvent thereby forming supercritical antisolvent, wherein said supercritical conditions include a temperature of 0.7-1.4 $T_c$ and a pressure of 0.2-7 $P_c$ for said antisolvent;
   with an ultrasonic device remote from the liquid containing material to be separated, generating ultrasonic energy waves within said near-supercritical or supercritical antisolvent in said chamber and propagating said waves through said near-supercritical or supercritical antisolvent in the interior of said chamber and into said containers thereby mixing said liquid and said supercritical antisolvent, supersaturating the liquid with the material to be separated, dissolving the liquid in the supercritical antisolvent, and precipitating the material as particles in said containers;
   flowing additional supercritical antisolvent through the chamber after precipitation of the material as particles in said containers;
   removing said antisolvent and liquid from said chamber and said containers, thereby leaving said particles in said containers; and
   reducing the pressure within said chamber to approximately atmospheric after said removing.

29. The method of claim 28 further comprising flushing the chamber with a fluid or inert gas following said removing.

30. The method of claim 28, wherein said material comprises a medicament.

31. The method of claim 30, wherein said liquid further comprises an auxiliary ingredient selected from the group consisting of adjuvant, excipient, extender, surface active agent, binder and a combination thereof.

32. The method of claim 28, wherein said antisolvent is selected from the group consisting of carbon dioxide, propane, butane, ethane, isobutane, nitrous oxide, sulfur hexafluoride, trifluoromethane, xenon, and mixtures thereof.

33. The method of claim 28, wherein said material comprises at least 5% by weight of said liquid.

34. The method of claim 28, wherein said particles have an average diameter of about 0.1-10 µm.

* * * * *